(12) United States Patent
Sekimoto et al.

(10) Patent No.: US 7,993,684 B2
(45) Date of Patent: Aug. 9, 2011

(54) METHOD OF INHIBITING ALVEOLAR BONE RESORPTION AND PERIODONTAL MEMBRANE LOSS AND COMPOSITION FOR INTERNAL USE TO BE USED THEREIN

(75) Inventors: Yukiyo Sekimoto, Takatsuki (JP); Hidehiko Otsuki, Takatsuki (JP); Akane Takemura, Takatsuki (JP)

(73) Assignee: Sunstar Inc., Osaka (JP)

( * ) Notice: Subject to any disclaimer, the term of this patent is extended or adjusted under 35 U.S.C. 154(b) by 0 days.

(21) Appl. No.: 12/781,062

(22) Filed: May 17, 2010

(65) Prior Publication Data

US 2010/0239689 A1 Sep. 23, 2010

Related U.S. Application Data

(62) Division of application No. 10/572,895, filed as application No. PCT/JP2004/014123 on Sep. 17, 2004, now abandoned.

(30) Foreign Application Priority Data

Sep. 19, 2003 (JP) ................................ 2003-328222

(51) Int. Cl.
*A01N 65/00* (2009.01)
(52) U.S. Cl. ...................................................... 424/725
(58) Field of Classification Search .......................... None
See application file for complete search history.

(56) References Cited

U.S. PATENT DOCUMENTS

| 2,943,938 | A | 7/1960 | De Zeeuw et al. |
| 5,424,331 | A | 6/1995 | Shlyankevich |
| 5,478,579 | A | 12/1995 | Sawruk |
| 6,670,343 | B1 | 12/2003 | Ito et al. |
| 6,881,419 | B2 | 4/2005 | Lovett |
| 2001/0010930 | A1 | 8/2001 | Obata et al. |

FOREIGN PATENT DOCUMENTS

| CA | 2 370 553 | 11/2000 |
| JP | 62-126186 | 6/1987 |
| JP | 04-283518 | 10/1992 |
| JP | 7-173148 | 7/1995 |
| JP | 8-133969 | 5/1996 |
| JP | 8-214787 | 8/1996 |
| JP | 11-9221 | 1/1999 |
| JP | 11-243910 | 9/1999 |
| JP | 11-269078 | 10/1999 |
| JP | 2000-139411 | 5/2000 |
| JP | 2001-213779 | 8/2001 |
| JP | 2001-213780 | 8/2001 |
| JP | 2002-121133 | 4/2002 |
| JP | 2002-121146 | 4/2002 |
| JP | 2002-179585 | 6/2002 |
| JP | 2002-363086 | 12/2002 |
| JP | 2002-542286 | 12/2002 |
| JP | 2003-55238 | 2/2003 |
| JP | 2003-95971 | 4/2003 |
| WO | 00/64438 | 11/2000 |
| WO | 01/05403 | 1/2001 |
| WO | 03/068218 | 8/2003 |

OTHER PUBLICATIONS

International Search Report mailed Nov. 22, 2004 in International (PCT) Application No. PCT/JP2004/014123.
Supplementary European Search Report dated Mar. 25, 2009 in corresponding European Application No. 04773435.5.
Roberto Civitelli, MD, et al., "Alveolar and Postcranial Bone Density in Postmenopausal Women Receiving Hormone/Estrogen Replacement Therapy", Archives of Internal Medicine, vol. 162, No. 12, Jun. 24, 2002, pp. 1-11.
T. Takano-Yamamoto, et al., "The Effect of Local Application of 1,25-Dihydroxycholecalciferol on Osteoclast Numbers in Orthodontically Treated Rats", Journal of Dental Research, vol. 71, No. 1, 1992, pp. 53-59.
Uchiwa, Tomoko, "A Radiological and Light and Electron Microscopic Study of Changes in the Alveolar Bone Due to Vitamin D Deficiency," The Journal of the Kyushu Dental Society, 46, 67-88, 1992 (English Abstract).
USDA-Iowa State University database on the isoflavone content of foods, 1999, 19 pages.
Franke, et al., "HPLC Analysis of Isoflavonoids and Other Phenolic Agents from Foods and from Human Fluids", Proceedings of the Society for Experimental Biology and Medicine 217: 263-273 (1998).
Kudou, et al., "Malonyl Isoflavone Glycosides in Soybean Seeds", Agric. Biol. Chem. 56(9): 2227-2233 (1991).
Soy & Health: The Healthful Balanced Nutrient (http://www.soyconnection.com/health_nutrition/pdf/Nutrients.pdf), retrieved on Sep. 15, 2008.
Shika Eiseishi, The Journal of Dental Hygienist, vol. 27, No. 9, pp. 16-23, (2003).
Japanese Office Action mailed Feb. 1, 2011 issued in corresponding Japanese Application No. 2005-515400 with English translation.
U.S. Office Action issued Dec. 27, 2007 in U.S. Appl. No. 10/572,895.
U.S. Office Action issued Jul. 17, 2008 in U.S. Appl. No. 10/572,895.
U.S. Advisory Action issued Oct. 2, 2008 in U.S. Appl. No. 10/572,895.
U.S. Office Action issued Nov. 18, 2008 in U.S. Appl. No. 10/572,895.
U.S. Office Action issued Jun. 30, 2009 in U.S. Appl. No. 10/572,895.
U.S. Office Action issued Feb. 19, 2010 in U.S. Appl. No. 10/572,895.
Kudou et al., Malonyl Isoflavone Glycosides in Soybean Seeds, Agric. Biol. Chem. 55(9): 2227-2233 (1991).
U.S. Restriction Requirement issued Nov. 6, 2007 in U.S. Appl. No. 10/572,895.

*Primary Examiner* — Michael Meller
(74) *Attorney, Agent, or Firm* — Wenderoth, Lind & Ponack, L.L.P.

(57) ABSTRACT

Alveolar bone resorption, periodontal membrane loss, and gingival recession can be inhibited by administering 500 mg to 2000 mg per day of calcium, 10 mg to 40 mg per day of soy isoflavone aglycone, and vitamin $D_3$ to persons having a tendency for decreased bone density, postmenopausal women, and periodontal disease patients in a maintenance phase; and even an extended period of administration provides a high degree of safety.

5 Claims, 2 Drawing Sheets

Change of MMP-8 level in gingival crevicular fluid (GCF) with time

METHOD OF INHIBITING ALVEOLAR BONE RESORPTION AND PERIODONTAL MEMBRANE LOSS AND COMPOSITION FOR INTERNAL USE TO BE USED THEREIN

This application is a Divisional of U.S. application Ser. No. 10/572,895, filed Mar. 20, 2006 (now abandoned), which is a national stage application of International application No. PCT/JP2004/014123, filed Sep. 17, 2004.

TECHNICAL FIELD

The present invention relates to a method for inhibiting alveolar bone resorption and periodontal membrane loss of persons having a tendency for decreased bone density, post-menopausal women, and periodontal disease patients in a maintenance phase; a method for inhibiting gingival recession of such persons; and an oral composition, an agent for preventing or treating gingival recession, and an agent for preventing or treating alveolar bone resorption and periodontal membrane loss, each comprising a soy isoflavone aglycone, calcium, and vitamin $D_3$.

BACKGROUND ART

Decreased bone density is caused by aging, nutrition/diet problems such as shortage of calcium intake, lack of exercise, medicines such as adrenal corticosteroids, etc. In particular, women tend to suffer a rapid decrease of bone mass because of decreased estrogen secretion due to menopause. Here, a person having decreased bone density is one whose bone mineral density is 1 SD (Standard Deviation) or more below the young adult mean (>−1 SD), according to the criteria proposed by the WHO research group in 1994; or one whose bone density is 80% or less of the young adult mean (YAM), according to the criteria proposed by the Japanese Society for Bone and Mineral Research in 1996.

Periodontal disease is an infection caused by specific periodontal disease-causing bacteria. Examples of such periodontal disease-causing bacteria include gram-negative anaerobic bacteria such as *Porphyromonas gingivalis*. Periodontal disease-causing bacteria increase in the plaque that forms around the root of a tooth cervix, inducing chronic inflammation of the surrounding tissues including gingiva, periodontal membrane, and alveolar bone, and thus developing symptoms of periodontal disease. Because of chronic inflammation induced by periodontal disease-causing bacteria, periodontal disease advances resorption of alveolar bone, which supports the teeth, and it is the greatest cause of lost teeth in developed countries.

With respect to postmenopausal women, it has been revealed that there is a correlation between the drop in bone density and the progression of periodontal disease (Yasunari Kurosu et al., Nihon Shika Hozongaku Zassi (The Japanese Journal of Conservative Dentistry), 1998), and decreased bone mass is regarded as a risk factor for periodontal disease.

The finding that a drop in bone density relates to the progression of periodontal disease led to an animal experiment using bisphosphonate, which is a bone resorption inhibitor. It was thus reported that bisphosphonate is useful for inhibiting alveolar bone resorption in experimental periodontitis (Reddy et al., J Periodontol, 66 (3), 211-217, 1995). However, since bisphosphonate has strong side effects, it is not suitable for periodontal disease treatment, which requires long-term medication. Therefore, the development of a pharmaceutical preparation having a high degree of safety has been desired.

Since periodontal tissues do not recover completely even after periodontal disease treatment, the dental root surface of a treated area is exposed. Because inflamed parts and affected tissues are physically removed in the process of treatment, the treated area tends to suffer gingival recession. Accordingly, in a maintenance phase, when the symptoms are stable after periodontal disease treatment, gingival recession and a relapse of periodontal disease are highly likely to occur. Therefore, the development of a pharmaceutical preparation that has a high degree of safety and that is useful for inhibiting gingival recession and maintaining periodontal tissues such as alveolar bone and periodontal membrane is desired.

It is well known that calcium is a necessary nutritional component for growing children, pregnant women, etc. to maintain or enhance the bone calcium density of alveolar bone ("X-ray, optical microscopic, and scanning electron microscopic research on alveolar bone changes due to vitamin D deficiency", The Journal of the Kyushu Dental Society, 46, 67-88, 1992). Accordingly, there are a large number of calcium food supplements available. It is known that specific calcium salts (such as calcium pantothenate) inhibit alveolar bone resorption, which is related to periodontal disease (Japanese Unexamined Patent Publication No. 1996-133969). It is thus accepted that intake of calcium and calcium salts is effective to some extent in the prevention of periodontal disease.

In contrast, it is known that soy isoflavones abundantly contain components having antibacterial properties and natural bone metabolism improvement actions. Therefore, soy isoflavones have been used together with calcium salts and vitamin D in oral nutritional supplements for osteoporosis prevention and whole-body bone strengthening, and, in the United States of America, they have been sold under the trade names of "Osteo Soy" (FreeLife, U.S.A.) and "Soylife" (Schouten, U.S.A.). Like ordinary calcium supplements, these are in oral tablet, capsule, and powder forms and are not intended for the prevention of periodontal disease. Among soy isoflavones, genistein shows antibacterial activity against periodontal disease-causing bacteria; therefore, it has been used as an antiperiodontitis agent (Japanese Unexamined Patent Publication No. 1992-283518) and has been used together with high-solubility calcium in a food composition for the prevention of periodontal disease or the prevention of periodontal disease progression (Japanese Unexamined Patent Publication No. 1999-243910). However, the above periodontal disease prevention is based on the antibacterial properties of soy isoflavones, and there has been no reported case of inhibited periodontal membrane loss.

DISCLOSURE OF THE INVENTION

An object of the present invention is to provide a method, oral composition, and prevention or treatment agent for inhibiting alveolar bone resorption and periodontal membrane loss or inhibiting gingival recession in persons having a tendency for decreased bone density and postmenopausal women, while having a high degree of safety even when the composition or agent is taken for extended periods of time.

The present inventors conducted extensive research and, as a result, found that alveolar bone resorption, periodontal membrane loss, and gingival recession can be inhibited by the combined use of a soy isoflavone aglycone, calcium, and vitamin $D_3$.

Based on this finding, the inventors have accomplished the present invention.

Specifically, the present invention provides the following oral compositions, prevention or treatment agents, and methods.

1. An oral composition for alveolar bone resorption inhibition and periodontal membrane loss inhibition, comprising a soy isoflavone aglycone, calcium, and vitamin $D_3$.
2. An agent for preventing or treating gingival recession, comprising a soy isoflavone aglycone, calcium, and vitamin $D_3$.
3. An agent for preventing or treating alveolar bone resorption and periodontal membrane loss, comprising a soy isoflavone aglycone, calcium, and vitamin $D_3$.
4. A composition or agent according to any one of items 1 to 3, wherein the proportion of soy isoflavone aglycone in the composition or agent is 0.001% to 10% by weight; and the proportion of calcium in the composition or agent is 0.01% to 50% by weight.
5. A composition or agent according to any one of items 1 to 3, wherein the composition or agent is for persons having decreased bone density, postmenopausal women, or periodontal disease patients in a maintenance phase.
6. A composition according to item 1, wherein the soy isoflavone aglycone is an extract from whole-grain soy; the genistein/daidzein weight ratio in the soy isoflavone aglycone is in the range of 1/1 to 1.5/1; and the proportion of the total weight of genistein and daidzein in the soy isoflavone aglycone is at least 90%.
7. A method for inhibiting alveolar bone resorption and periodontal membrane loss, comprising orally administering a composition according to any one of items 1 to 6.
8. A method for preventing or treating gingival recession, comprising orally administering a soy isoflavone aglycone, calcium, and vitamin $D_3$.
9. A method for preventing or treating alveolar bone resorption and periodontal membrane loss, comprising orally administering a soy isoflavone aglycone, calcium, and vitamin $D_3$.
10. A method according to item 8 or 9, wherein the soy isoflavone aglycone, calcium, and vitamin $D_3$ are administered to persons having decreased bone density, postmenopausal women, or periodontal disease patients in a maintenance phase.
11. A method according to item 9 or 10, wherein the soy isoflavone aglycone is administered in an amount of 10 mg to 40 mg per day; and calcium is administered in an amount of 500 mg to 2000 mg per day.

In the present specification, gingival recession includes a gingival margin receding down from the boundary between the tooth cementum and enamel, i.e., the cement/enamel junction, toward the root apex, thereby exposing a dental root. Gingival recession can be quantified by, for example, the numerical value obtained by subtracting the periodontal pocket depth (PD) from the clinical attachment level (CAL) (see FIG. 1). In the present specification, periodontal disease patients in a maintenance phase encompass those who, having finished periodontal disease treatment, are in a clinically recovered and stable condition but need observation.

Soy isoflavone aglycones in the present invention are soy isoflavone nonglycosides such as genistein, daidzein, glycitein, etc., and can be usually obtained as soy isoflavone glycoside hydrolysates. Such soy isoflavone aglycones can be obtained by, for example, extracting a glycoside from seeds (whole-grain soybeans) of *Glycine max Merrill* (Leguminosae family) according to such a known method as disclosed in Japanese Unexamined Patent Publication No. 1987-126186, and subjecting the obtained glycoside to acid heating or β-glucuronidase enzyme hydrolysis in a purification step.

There are no limitations on the methods for obtaining soybean extracts from whole-grain soybeans or isoflavone glycosides from ground soybeans, and obtaining aglycones from the glycosides. If soybean hypocotyls are used instead of whole-grain soybeans, isoflavones can be efficiently obtained; however, the content of glycosides such as daidzin, glycitin, etc., is high, and such glycosides are not easily converted into nonglycosides such as genistein, daidzein, etc. by hydrolysis. Therefore, whole-grain soybeans are more advantageous than soybean hypocotyls as starting materials for soy isoflavone aglycones such as genistein, daidzein, etc.

The soy isoflavone aglycone used in the present invention is preferably at least one aglycone selected from the group consisting of genistein and daidzein. It is preferable to use genistein and daidzein in combination such that the genistein/daidzein weight ratio is in the range of 1/1 to 1.5/1. In the soy isoflavone aglycone, the content of genistein is preferably greater than that of daidzein. It is also preferable that the proportion of the total weight of genistein and daidzein in the soy isoflavone aglycone is at least 90% by weight. Soy isoflavone aglycones may be powdered with excipients added thereto to be in forms suitable for various oral preparations or may be used in forms suitable for beverages, such as preparations with emulsifiers and solubilizers added thereto, cyclodextrin inclusion preparations, etc.

The proportion of soy isoflavone aglycone in the composition or the prevention/treatment agent of the present invention is not limited as long as it allows the objects of the invention to be achieved. The proportion of soy isoflavone aglycone in the composition or the prevention/treatment agent of the invention is usually 0.001% to 10% by weight, and preferably 0.005% to 5.0% by weight. In the method for inhibition of alveolar bone resorption and periodontal membrane loss and the method for prevention or treatment thereof according to the present invention, soy isoflavone aglycone is usually administered to an adult in an amount of 10 mg to 40 mg per day, and preferably in an amount of 10 mg to 20 mg per day; and the administration of soy isoflavone aglycone may be carried out in one dose a day or in two or more divided doses a day.

Any natural or synthetic calcium may be used in the present invention. Examples of natural forms of calcium include those derived from oyster shells, egg shells, corals, cattle bones, milk, etc.; and these items themselves and crude products of these such as ground products, dried products, etc, can be used as calcium sources. Examples of synthetic forms of calcium include calcium gluconate, calcium lactate, calcium chloride, calcium glycerophosphate, calcium pantothenate, calcium tertiary phosphate, calcium carbonate, calcium citrate, etc. Such forms of calcium may be used singly or in combination of two or more.

The proportion of calcium in the composition or the prevention/treatment agent of the present invention is not limited as long as it allows the objects of the invention to be achieved. The proportion of calcium in the composition or the prevention/treatment agent of the invention is usually 0.01% to 50% by weight, and preferably 0.1% to 20% by weight, calculated as the Ca content. In the method for inhibition of alveolar bone resorption and periodontal membrane loss and the method for prevention or treatment thereof according to the present invention, calcium is usually administered to an adult in an amount of 500 mg to 2000 mg per day, and preferably in an amount of 500 mg to 1000 mg per day; and the administration of calcium may be carried out in one dose a day or in two or more divided doses a day.

Vitamin $D_3$, which is used in the present invention, is also called cholecalciferol. When used in the composition or the prevention/treatment agent of the invention, vitamin $D_3$ may be in crystalline form or may be in the form of a preparation for stabilization. The proportion of vitamin $D_3$ in the composition or the prevention/treatment agent of the present invention is not limited as long as it allows the objects of the invention to be achieved. The proportion of vitamin $D_3$ in the composition or the prevention/treatment agent of the invention is usually $10^{-8}\%$ to $10^{-1}\%$ by weight, and preferably $10^{-7}\%$ to $10^{-2}\%$ by weight. In the method for inhibition of alveolar bone resorption and periodontal membrane loss and the method for prevention or treatment thereof according to the present invention, vitamin $D_3$ is usually administered to an adult in an amount of 200 IU to 800 IU per day, and preferably in an amount of 200 IU to 400 IU per day; and the administration of vitamin $D_3$ can be carried out in one dose a day or in two or more divided doses a day.

The composition of the present invention is an oral composition for alveolar bone resorption inhibition and periodontal membrane loss inhibition. Examples of oral compositions include food compositions, pharmaceutical compositions, etc.; and preferable examples thereof are food compositions. The forms of oral compositions of the present invention encompass those used in the fields of foods and pharmaceuticals; however, preferable forms are those which allow the composition to stay in the oral cavity for a long time, such as troches, chewing gums, chewable tablets, gummy candies, candies, etc. Among such forms, troches and chewable tablets are especially preferable. Tablets such as troches and chewable tablets are preferably produced by the following method.

A powder mixture (powder particle diameter: no more than 250 μm) of soy isoflavone aglycone with other components such as calcium, sugar alcohol, and excipient are wetted by alcohol, water, and optionally a disaccharide-or-higher polymerized reducing sugar such as polydextrose, reduction dextrin, maltitol, maltotriitol, etc. or a combination of such disaccharide-or-higher polymerized reducing sugars, and granulated. The resulting granules are mixed with flavor, vitamin $D_3$ preparation, lubricant, useful components that are sensitive to heat or moisture, etc. as needed, and tableted. The resulting tablets were then formed into tablets having a diameter of 12 mm to 20 mm, a thickness of 3 mm to 6 mm, and a weight of 500 mg to 3000 mg per tablet, using a rotary tableting machine. The tablet hardness as measured in the diameter direction using a Kiya hardness tester is preferably within the range of 5 kg to 15 kg, and most preferably within the range of 7 kg to 13 kg.

The prevention/treatment agent of the present invention is useful for preventing or treating alveolar bone resorption and periodontal membrane loss or for preventing or treating gingival recession, and the agent comprises a soy isoflavone aglycone, calcium, and vitamin $D_3$ as effective components. The form of the prevention/treatment agent of the invention is not limited as long as it is suitable for oral ingestion, and the prevention/treatment agent may be, for example, in forms that can be used for oral ingestion in foods, pharmaceuticals, etc.

The oral composition and the prevention/treatment agent of the present invention may contain additives typically used in foods, such as pH adjusters, organic acids, sugar alcohols, sweeteners, flavors, dental plaque formation inhibiting materials, and bad breath inhibiting materials; edible additives used in pharmaceuticals, such as excipients, other effective components, and carriers; etc. as needed, as long as the effects of the present invention are not impaired thereby. Examples of materials for such additives include phosphates, malic acid, citric acid, lactic acid, pantothenic acid, sugar alcohols such as sorbitol, xylitol, erythritol, palatinit, palatinose, maltitol, and reducing starch sugars, isomerized sugars such as reducing isomaltooligosaccharides, gum bases, gum arabic, gelatin, cetyl methyl cellulose, sodium saccharin, aspartame, magnesium stearate, granulated sugar, powdered sugar, starch syrup, microcrystalline cellulose, 1-menthol, D-group vitamins other than vitamin $D_3$, K-group vitamins such as vitamin K, vitamin P, lysine, magnesium salts, calcitonin, ipriflavone, etc. The amounts of such additives are not limited and can be suitably determined in accordance with the purpose of use, etc.

The method for inhibiting alveolar bone resorption and periodontal membrane loss according to the present invention comprises orally administering at least one member selected from the group consisting of the above oral compositions and prevention/treatment agents. The method for preventing or treating gingival recession and the method for preventing or treating alveolar bone resorption and periodontal membrane loss according to the present invention comprise orally administering a soy isoflavone aglycone, calcium, and vitamin $D_3$.

In these methods, the subject for administration is not limited as long as it is a mammal; however, preferable subjects for administration are persons having decreased bone density, postmenopausal women, and periodontal disease patients in a maintenance phase. A person having decreased bone density is one whose bone mineral density is 1 SD (Standard Deviation) or more below the young adult mean ($>-1$ SD).

The administration amount, form, etc. of the oral composition and the prevention/treatment agent of the present invention are described above.

BEST MODE FOR CARRYING OUT THE INVENTION

The present invention is described below in more detail with reference to Examples and Test Examples. However, the present invention is not limited to these examples. In these examples, percentages are by weight unless otherwise indicated.

TEST EXAMPLE 1

Test for Bone Resorption Inhibition and Periodontal Membrane Loss Inhibition Using Periodontal Maintenance Patients 1. Test Subjects The test subjects were 50 women periodontal disease patients at least one year after menopause. In selecting the test subjects, it was confirmed that they did not have any critical systemic underlying disease, were not under hormone replacement therapy or osteoporosis medicine treatment, and, within the past three months, had not undergone surgical periodontal treatment or antibiotic medication. The 50 test subjects were randomly assigned to two groups: a test group and a placebo group.

2. Test Pharmaceutical Preparation
Prescription of Test Pharmaceutical Preparation:

| | |
|---|---|
| Non-calcinated shell calcium | 650 mg (calcium content: 250 mg) |
| Soy isoflavone extract (containing 5 mg of soy isoflavone aglycon) (genistein:daidzein = 1.3:1) | 17 mg |
| Vitamin $D_3$ | 2.5 μg (100 IU) |
| Sugar alcohol | Balance |
| Sweetener, Flavor, etc. | 140 mg |
| Total | 2000 mg/tablet |

3. Test Method

The subjects ingested two tablets of the test pharmaceutical preparation after breakfast for 24 weeks. At the time of tablet distribution (hereinafter referred to as baseline), and in the 12th and 24th weeks after the start of tablet ingestion, they were subjected to inquiries, standard X-ray photography of the oral cavity, periodontal tissue examination, and sampling of gingival crevicular fluid (hereinafter referred to as GCF) for biochemical marker measurement. The amounts of Ca and soy isoflavone daidzein and genistein that the subjects ingested from foods, etc. were calculated from meal records by registered dietitians.

4. Periodontal Tissue Examination

1) Periodontal Pocket Depth (Hereinafter Referred to as PD) and Clinical Attachment Level (Hereinafter Referred to as CAL)

Figure 1:
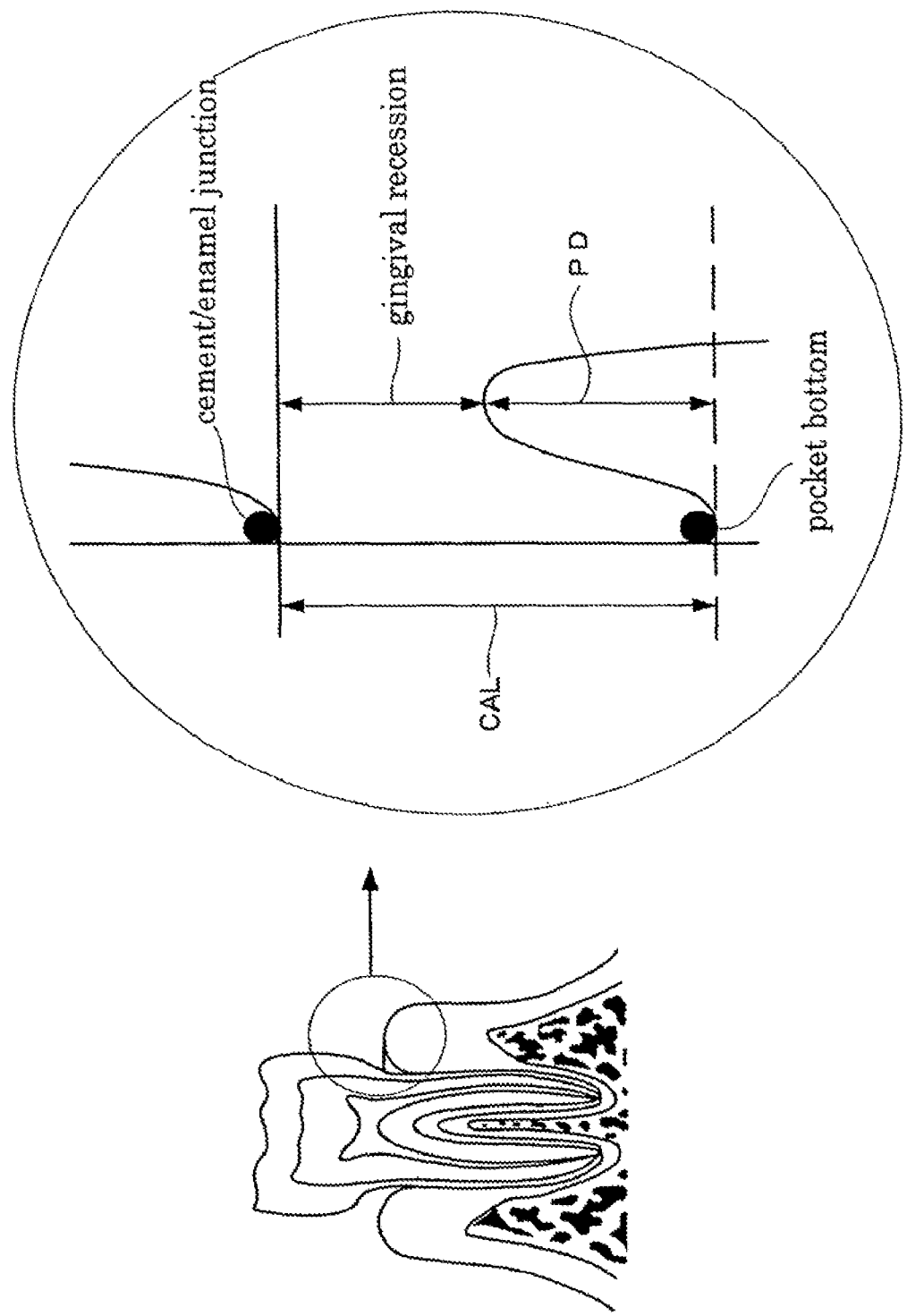
FIG. 1 is a sectional view of a tooth crown, dental root, and periodontal tissue, showing the relationship between CAL, PD, and gingival recession.

PD and CAL of all the teeth except the third molars were measured in units of 0.5 mm by the six-point method, using a 15 mm probe (UNC15, Hu-Friedy, USA) with a scale graduated in 1 mm increments. CAL is the distance from the cement/enamel junction to the periodontal pocket bottom (see FIG. 1).

2) Gingival Recession

Gingival recession was indicated by the numerical value obtained by subtracting the PD from the CAL at each point.

3) Alveolar Bone Height (Hereinafter Referred to as ACH)

Standard X-ray photography was performed on the molar sites on both sides by the bite wing method, and the distance from the cement/enamel junction to the alveolar bone crest along the dental root surface was measured by the same skilled person.

5. Measurement of Biochemical Marker in GCF

GCF was sampled from mesiobuccal sites of the third molars on the upper jaw right side and the lower jaw left side, using periopaper (Proflow™ Incorporated, USA). Periopaper was inserted to the bottom of a pocket, left for 10 seconds, taken out to measure the amount of GCF by a Periotron 8000 (Harco Electronics, USA). After periopaper was placed into a microtube, it was used to measure matrix metalloprotease-8 (hereinafter referred to as MMP-8), which is an index of connective tissue damage. After extraction processing with Tris chloride buffer solution (pH 7.6), MMP-8 was measured using MMP-8 Human Biotrak ELISA System (Amersham Biosciences, USA). The whole amount of MMP-8 of each GCF sample was calculated from the measurement results.

6. Statistics Analysis

The subjects' background factors, ACH, PD, CAL, and gingival recession were all analyzed by a one-way layout analysis of variance (ANOVA) and subsequent multiple comparison test. PD and CAL values were used for analysis, with the figure at the first decimal place being ignored. Change with time within group was analyzed by a Bonferroni-correction nonparametric test. For all analyses, a two-sided significance level of 5% was applied.

7. Results

1) General Condition

No significant differences were recognized between groups in terms of background factors: age, BMI, menopause age, the number of years after menopause, the number of smokers, the number of teeth present, and the average amounts of ingestion of Ca, daidzein, and genistein from foods during the test period.

2) Periodontal Tissue Examination

No significant differences were recognized between the groups in terms of the subject average values of CAL, gingival recession, and ACH at the time of baseline.

2-1) CAL

Table 1 shows CAL average values and average rates of change (which are obtained by dividing the amount of change in the CAL average value at 12 or 24 weeks by the baseline CAL average value). In both groups, areas that had at least 3 mm CAL at the time of baseline, when they were under maintenance care after treatment, showed significant CAL decrease from the baseline at the 12th and 24th weeks. In order to adjust for the difference between the groups at the time of baseline, analysis was conducted on the CAL average rates of change obtained by dividing the amount of change in CAL at 12 or 24 weeks by the baseline CAL value. As the result, in comparison with the placebo group, the test group showed significant improvement in CAL at the 24th week.

TABLE 1

| | CAL average value(mm) | | | CAL rate of change(%) | |
|---|---|---|---|---|---|
| Group | Baseline | 12th week | 24th week | Δ12 weeks | Δ24 weeks |
| Test group | 3.90 | 3.42 | 3.34 | −12.5 | −14.2 |
| Placebo group | 4.08 | 3.75 | 3.74 | −8.9 | −8.9 |

2-2) Gingival Recession

Table 2 shows gingival recession average values and rates of change (which are obtained by dividing the amount of change in the gingival recession average value at 12 or 24 weeks by the baseline gingival recession average value). In the test group and the placebo group, areas that had gingival recession at the beginning of the test showed significant improvement in gingival recession at the 12th and 24th weeks. However, the test group showed significant difference from the placebo group in the gingival recession rate of change at the end of the test.

TABLE 2

| | Gingival recession average value(mm) | | | Gingival recession rate of change(%) | |
|---|---|---|---|---|---|
| Group | Baseline | 12th week | 24th week | Δ12 weeks | Δ24 weeks |
| Test group | 1.70 | 1.19 | 1.08 | −30.1 | −37.8 |
| Placebo group | 1.97 | 1.74 | 1.74 | −15.0 | −16.4 |

2-3) ACH

Table 3 shows ACH rates of change (which are obtained by dividing the amount of change in the ACH average value at 12 or 24 weeks by the baseline ACH average value). In order to adjust for the difference between the groups at the time of baseline, analysis was conducted on the ACH average rates of change obtained by dividing the amount of change in ACH at 12 or 24 weeks by the baseline ACH value. As the result, in comparison with the placebo group, the test group showed a tendency to inhibit ACH and, in particular, there was significant difference from the placebo group at the 12th week.

TABLE 3

| Group | ACH rate of change(%) | |
|---|---|---|
| | Δ12 weeks | Δ24 weeks |
| Test group | 0.3 | 0.3 |
| Placebo group | 7.1 | 9.5 |

2-4) Level of MMP-8 in GCF

Figure 2:
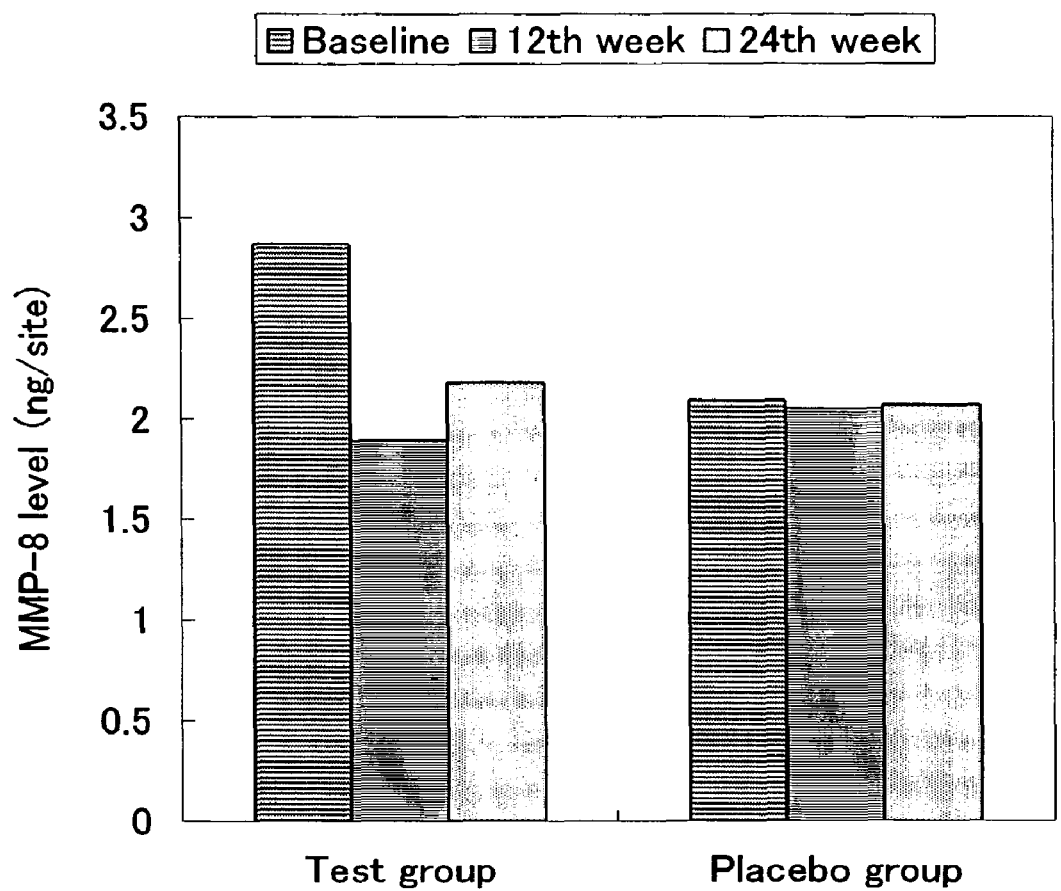
FIG. 2 is a graph showing the change of MMP-8 level with time in the gingival crevicular fluid (GCF) obtained in Test Example 1.

FIG. 2 shows the MMP-8 average values at the time of baseline, the 12th week, and the 24th week. The placebo group did not show any changes, while the test group showed significant decreases from the baseline at the 12th and 24th weeks.

The above test results reveal the following points.

The present test pharmaceutical preparation promoted improvement in the CAL of postmenopausal periodontal disease patients in a maintenance phase. It was thus found that the pharmaceutical preparation has the action of improving connective tissue attachment by the periodontal membrane, that is, the normal periodontal tissue attachment obtained by the periodontal membrane lying between the alveolar bone and dental root surface (cementum). Since the present test pharmaceutical preparation inhibited the level of MMP-8, it was found that the pharmaceutical preparation has the action of preventing loss of connective tissue mainly composed of periodontal membrane, thus being useful for inhibiting periodontal membrane loss.

Although alveolar bone resorption tends to make rapid progress in postmenopausal women, the present test group showed an inhibited increase in ACH in comparison with the placebo group. An effect of inhibiting alveolar bone resorption was thus found.

Although gingival recession tends to occur easily in treated areas, it was improved in the present test. It was thus found that not only a relapse of periodontal disease but also dental root surface caries and hypersensitivity due to exposed roots can be prevented and/or improved, and that aesthetic aspects can also be improved.

EXAMPLE 1

Granule (Ingestion: 4 g per Day)

Granules were produced by a standard method, using the following components:

| Component | Amount (%) |
|---|---|
| Whey calcium (calcium content: 26%) | 50.00 |
| Soy isoflavone extract (aglycon content: 30%) (genistein:daidzein = 1.5:1) | 1.00 |
| Oil-soluble licorice extract | 1.00 |
| Vitamin $D_3$ (vitamin $D_3$ content: 0.25%) | 0.05 |
| Xylitol | 40.00 |
| Palatinit | Balance |
| Aspartame | 0.10 |
| Gum arabic | 1.00 |
| Flavor | 2.50 |
| Total | 100.00 |

EXAMPLE 2

Intraoral Solution Tablet (Ingestion: 4 g per Day)

Intraoral solution tablets were produced by a standard method, using the following components:

| Component | Amount (%) |
|---|---|
| Oyster shell calcium (calcium content: 39%) | 35.00 |
| Soy isoflavone extract (aglycon content: 70%) (genistein:daidzein = 1.3:1) | 0.5 |
| Palatinit | Balance |
| Maltitol | 30.00 |
| Vitamin $D_3$ (vitamin $D_3$ content: 0.25%) | 0.05 |
| Polydextrose | 5.00 |
| Sucrose fatty acid ester | 4.00 |
| Cocoa powder | 5.00 |
| Sucralose | 1.00 |
| Flavor | 2.50 |
| Total | 100.00 |

EXAMPLE 3

Intraoral Solution Tablet (Ingestion: 4 g per Day)

Intraoral solution tablets were produced by a standard method, using the following components:

| Component | Amount (%) |
|---|---|
| Calcium tertiary phosphate (calcium content: 39.1%) | 35.00 |
| Soy isoflavone extract (aglycon content: 33%) (genistein:daidzein = 1.3:1) | 1.50 |
| Vitamin K | 0.01 |
| Vitamin $D_3$ preparation (vitamin $D_3$ content: 0.25%) | 0.1 |
| Xylitol | 31.00 |
| Palatinit | Balance |
| Citric acid | 0.50 |
| Gum Arabic | 1.20 |
| Magnesium stearate | 1.00 |
| Flavor | 3.00 |
| Total | 100.00 |

EXAMPLE 4

Chewing Gum (Ingestion: 20 g per Day; 40% of Soy Isoflavone Eluted; 85% of Calcium Eluted; and 40% of Vitamin $D_3$ Eluted)

A chewing gum was produced by a standard method, using the following components:

| Component | Amount (%) |
|---|---|
| Calcium gluconate-calcium lactate amorphous material (calcium content: 10%) | 30.00 |
| Tea extract | 0.05 |

-continued

| Component | Amount (%) |
|---|---|
| Soy isoflavone extract (aglycon content: 70%) (genistein:daidzein = 1.3:1) | 0.25 |
| Gum base | 27.00 |
| Erythritol | 10.00 |
| Xylitol | 38.00 |
| Vitamin $D_3$ (vitamin $D_3$ content: 0.25%) | 0.0001 |
| Reducing malt sugar syrup | Balance |
| Flavor | 5.00 |
| Total | 100.00 |

EXAMPLE 5

Candy (Ingestion: 30 g per Day)

A candy was produced by a standard method, using the following components.

Oyster shell calcium, xylitol, oil-soluble licorice extract, tea polyphenol extract, vitamin $D_3$, and powder flavor were incorporated in the center of the candy in powdered forms.

| Component | Amount (%) |
|---|---|
| Oyster shell calcium (calcium content: 39%) | 5.00 |
| Oil-soluble licorice extract | 0.05 |
| Soy isoflavone extract (aglycon content: 70%) (genistein:daidzein = 1.3:1) | 0.1 |
| Xylitol | 5.00 |
| Tea polyphenol extract | 0.05 |
| Palatinit | Balance |
| Maltitol | 10.00 |
| Aspartame | 0.04 |
| Citric acid | 0.50 |
| Oil flavor | 0.20 |
| Powder flavor | 0.30 |
| Vitamin $D_3$ (vitamin $D_3$ content: 0.25%) | 0.0001 |
| Total | 100.00 |

EXAMPLE 6

Troche (Ingestion: 8 g per Day)

A troche was produced by the standard method, using the following components:

| Component | Amount (%) |
|---|---|
| Citrate calcium (calcium content: 21%) | 10.00 |
| Calcium tertiary phosphate (calcium content: 39%) | 15.00 |
| Soy isoflavone extract (aglycon content: 70%) (genistein:daidzein = 1:1) | 0.25 |

-continued

| Component | Amount (%) |
|---|---|
| Vitamin $D_3$ (vitamin $D_3$ content: 0.25%) | 0.05 |
| Palatinit | 33.00 |
| Xylitol | Balance |
| Sodium carboxymethylcellulose | 1.00 |
| Citric acid | 2.00 |
| Malic acid | 1.00 |
| Aspartame | 0.50 |
| Sucrose fatty acid ester | 4.00 |
| Flavor | 2.00 |
| Total | 100.00 |

EXAMPLE 7

Drink Formulation (Ingestion: 100 ml per Day)

A drink formulation was produced by a standard method, using the following components:

| Component | Amount |
|---|---|
| Fermentation lactic acid (50% aqueous solution) | 0.97 g |
| Gluconic acid (50% aqueous solution) | 3.88 g |
| Calcium gluconate-calcium lactate amorphous material (calcium content: 10%) | 5.00 g |
| Soy isoflavone aglycon-β cyclodextrin inclusion material (aglycon content: 3%) (genistein:daidzein = 1.5:1) | 0.350 g |
| Erythritol | 7.00 g |
| Sucralose | 0.03 g |
| Stevia | 0.01 g |
| Vitamin $D_3$ (vitamin $D_3$ content: 0.2%) | 0.003 g |
| Purified water | Balance |
| Total | 100 ml |

The invention claimed is:

1. A method for treating gingival recession in a patient, comprising orally administering a composition comprising therapeutically effective amounts of a soy isoflavone aglycone, calcium, and vitamin $D_3$, to said patient,
wherein the soy isoflavone aglycone contains genistein and daidzein, and has a genistein/daidzein weight ratio in a range of 1/1 to 1.5/1.

2. The method according to claim 1, wherein the proportion of the total weight of genistein and daidzein in the soy isoflavone aglycone is at least 90%.

3. The method according to claim 1, wherein the proportion of the soy isoflavone aglycone in the composition is 0.001% to 10% by weight.

4. The method according to claim 1, wherein the patient is a periodontal disease patient in a maintenance phase.

5. The method according to claim 1, wherein the soy isoflavone aglycone is administered in an amount of 10 mg to 40 mg per day; and calcium is administered in an amount of 500 mg to 2000 mg per day.

* * * * *